United States Patent

Müller et al.

[11] Patent Number: 5,536,244
[45] Date of Patent: Jul. 16, 1996

[54] ENDOSCOPIC INSTRUMENT WITH IMPROVED CLOSURE WINDOW

[75] Inventors: Werner Müller, Oetisheim; Bernd Pfitzenmeier, Bretten-Gölshausen; Ralf Thiehofe, Bretten-Diedelsheim, all of Germany

[73] Assignee: Richard Wolf GmbH, Knittlingen, Germany

[21] Appl. No.: 266,294

[22] Filed: Jun. 27, 1994

[30] Foreign Application Priority Data

Jun. 26, 1993 [DE] Germany .................. 93 09 545.7 U

[51] Int. Cl.⁶ .................................................. A61B 1/00
[52] U.S. Cl. ........................................... 600/176; 600/133
[58] Field of Search ................. 128/4–10; 385/115, 385/117, 118, 119; 600/176, 177, 175, 162, 133

[56] References Cited

U.S. PATENT DOCUMENTS

| | | |
|---|---|---|
| 3,417,745 | 12/1968 | Sheldon . |
| 4,170,997 | 10/1979 | Pinnow et al. ............... 128/4 X |
| 4,583,539 | 4/1986 | Karlin et al. ............... 606/11 X |
| 4,677,471 | 6/1987 | Takamura et al. ............ 128/6 X |
| 4,779,130 | 10/1988 | Vabe ............................. 128/6 X |
| 4,779,613 | 10/1988 | Hashiguchi et al. ............ 128/6 |
| 4,905,082 | 2/1990 | Nishigaki et al. ............ 128/6 X |
| 4,942,867 | 7/1990 | Takahashi et al. . |
| 5,056,902 | 10/1991 | Chinnock et al. .............. 128/4 X |

FOREIGN PATENT DOCUMENTS

| | | |
|---|---|---|
| 2062178 | 6/1972 | Germany . |
| 3139837 | 4/1983 | Germany . |
| 3740416 | 6/1989 | Germany . |
| 3740417 | 6/1989 | Germany . |
| 9016629 | 4/1991 | Germany . |

*Primary Examiner*—Richard J. Apley
*Assistant Examiner*—John P. Leubecker
*Attorney, Agent, or Firm*—Panitch Schwarze Jacobs & Nadel

[57] ABSTRACT

An endoscopic instrument includes an elongate shaft with an optical system arranged therein. The shaft is closed off at least its distal end by a window which is firmly and tightly connected to the shaft. The closure window is constructed of spinel or yttrium-aluminum-garnet. The spinel may be cubic monocrystalline spinel or polycrystalline spinel, and the yttrium-aluminum-garnet may be undoped or neodymium-doped. Similar closure windows of the same materials may be provided at other openings in the endoscope shaft, such as a proximal end ocular or eyepiece or a lateral light guide window. The closure window may optionally be in the form of a lens to function as part of the optical system.

17 Claims, 2 Drawing Sheets ic instrument with
improved closure window

FIELD OF THE INVENTION

The invention relates to an endoscopic instrument having an elongated shaft with an optical observation system arranged therein. The observation system is closed off at the distal end of the shaft by a window which is connected firmly and tightly with the shaft.

BACKGROUND OF THE INVENTION

Endoscopic instruments of this type are frequently used in medicine and serve for the observation, examination and treatment of body cavities either using a natural body orifice or an artificially created incision channel. All endoscopic instruments have in common an optical observation system which is closed off at the distal shaft end by a window. This window is connected tightly and firmly with the shaft. If this is not a video endoscope, an eyepiece is provided, as a rule, at the proximal end of the instrument. Furthermore, an illuminating system can be associated with the optical observation system; then a fiber optic light guide connector is additionally provided in the proximal region of the shaft.

Usually, the closure windows of such endoscopic instruments consist of glass. Although the concern with regard to the optical components lying inside the shaft involves almost exclusively their imaging characteristics, further requirements are placed on a closure window, in particular of a mechanical and material nature. On the one hand, as great a hardness as possible is desired for the closure window, in order to largely rule out impairment by possible scratches. On the other hand, in addition to this abrasive resistance, care must also be taken that sterilization is possible without loss of optical quality. Thus, for example, with an established sterilization cycle, the endoscopic instrument is exposed for a predetermined period to $H_2O$ saturated superheated steam at a temperature of 134° C.

Only a few types of glass are suitable for such sterilization cycles, and even these only with limitations. The reason for this is that, as is known, at high temperatures certain water-soluble substances are washed out from the surface of the glass, which leads to loss of optical quality. Also corrosion phenomena on the exterior glass surfaces are brought about through repeated sterilization, which are due essentially to the reciprocal effect of the metallic oxides contained in the glass with the water vapor. Substances indeed exist which are similar to glass, with a partially amorphous structure, which can cope with this stress, but these cannot be used for optical purposes owing to intense inhomogeneities.

Better results are achieved, on the other hand, with monocrystalline sapphire as a material for the closure window. The use of such a material is described for example in DE 37 40 416 A1. A crystalline sapphire has a high level of surface hardness and can be readily exposed to the sterilization cycles described above, but owing to its hexagonal crystal lattice, this material displays an anisotropic behavior for various optical and physical characteristics which are particularly undesirable for use in endoscope optical systems. Here, especially, the problem of double refraction is to be stressed.

The refractive indices of this material have between the axis parallel to the crystal axis and the vertical a difference on the order of $9\times10^{-3}$. In light beams which enter the crystal obliquely to the optical axis of the crystal, this double refraction causes a splitting into two polarized partial beams which extend vertically with respect to each other. It is therefore an indispensable requirement in the production and incorporation of closure windows of sapphire to pay precise attention to the orientation of the crystal. This is very costly in terms of manufacturing technology.

However, even with attention being paid to the crystal orientation and the prescribed production and incorporation of such a closure window, it is not possible, apart from the parallel light passage, to completely circumvent the effect of double refraction. In fact, owing to the necessary large field of vision in connection with small system diameters in endoscopic optics, very large apertures are necessary. This leads to the beams passing through the window in a large angle range, whereby differences in refractive index also make themselves apparent in practice. This results in a non-correctable loss of image quality.

SUMMARY OF THE INVENTION

Proceeding from this background, the invention is based on the problem of constructing an endoscopic instrument of the type mentioned in the Filed of the Invention such that the positive characteristics of sapphire as a closure window are largely retained, but the problem of double refraction is solved.

This problem is solved according to the invention by constructing the closure window of spinel or yttrium-aluminum-garnet. These materials have a hardness similar to sapphire, and are therefore substantially more wear-resistant than optical glasses; they are resistant to water and various acids, even at the high temperatures mentioned above, but they do not display any double refraction.

In order to be able to subject the entire endoscopic instrument to the superheated steam sterilization cycle mentioned above, it is expedient not only to provide the distal closure window but also, if present, the proximal eyepiece and also, if applicable, the light guide connector, with such a closure window of spinel or yttrium-aluminum-garnet and hence to hermetically seal the entire optical observation system and also, if applicable, the entire illumination system.

With the use of spinel, both cubic monocrystalline spinel ($MgO_xAl_2O_3$) and also polycrystalline spinel ($MgAl_2O_4$) can be used. The latter material likewise has excellent characteristics for the above purposes and is particularly useful for closure windows having small dimensions and low mean thickness.

With the use of yttrium-aluminum-garnet as a closure window, owing to its optical characteristics, preferably undoped yttrium-aluminum-garnet ($Y_3Al_5O_2$) is used in cubic monocrystaline form. However, doped material may also possibly be used, preferably neodymium-doped yttrium-aluminum-garnet known from laser technology.

In order to achieve as tight and hermetic a closure of the optical system as possible, it is important to incorporate the closure window or windows into the instrument so as to be effectively locked as far as possible by the material holding it. In the simplest form, this may take place by adhering. The adhesives currently available on the market, however, are not sufficiently resistant, in particular for the above-mentioned superheated steam sterilization cycles, so that currently a soldering/welding method is to be preferred. Here, the closure window can first be metallized (i.e., given a metallic coating on the edge and then soldered into the instrument, in particular into the shaft.

Preferably, however, the closure window is soldered into a metallic frame directly under a high vacuum. Thereafter, the frame with the window situated therein is connected firmly and tightly with the instrument, preferably by welding, in particular electron beam welding, or by soft soldering (temperatures approximating 200° to 250° C.). This method is of great advantage, in particular, in terms of manufacturing technique, because for the purpose of high vacuum soldering, which is technically comparatively costly, in each case only the frame and the closure window itself are to be handled, while only in a further processing step, which is comparatively simple, is the window together with the frame connected to the instrument by welding.

BRIEF DESCRIPTION OF THE DRAWINGS

The foregoing summary, as well as the following detailed description of preferred embodiments of the invention, will be better understood when read in conjunction with the appended drawings. For the purpose of illustrating the invention, there is shown in the drawings an embodiment which is presently preferred. It should be understood, however, that the invention is not limited to the precise arrangements and instrumentalities shown. In the drawings.

DETAILED DESCRIPTION OF PREFERRED EMBODIMENTS

Figure 1:
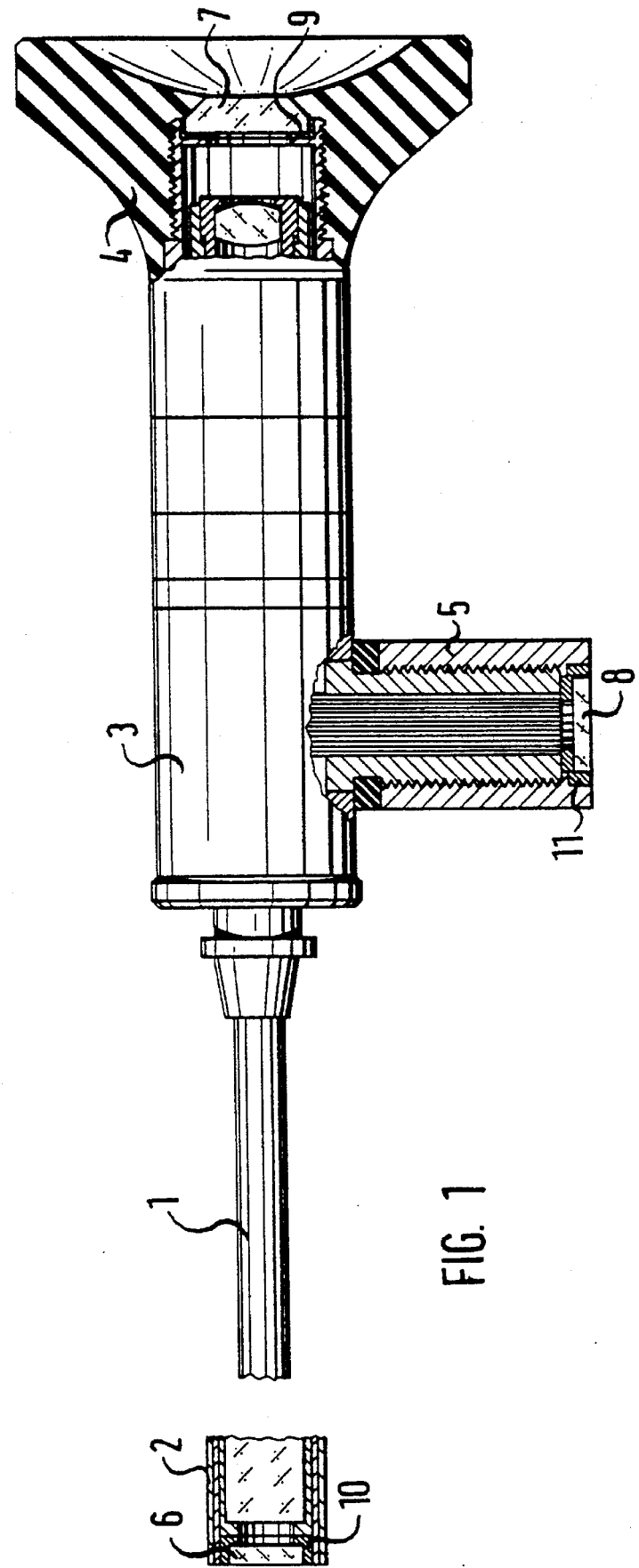
FIG. 1 shows a diagrammatic representation of an endoscopic instrument, represented partially in section and partially enlarged, in side view.

The endoscopic instrument illustrated with the aid of FIG. 1 is provided exclusively for observation purposes; it has an elongated shaft 1, the distal end region 2 of which is illustrated in section and on an enlarged scale. On the proximal side, a handle piece 3 joins the shaft 1, which handle piece 3 is closed off in the proximal direction by the ocular or eyepiece 4. A fiber optic light guide connector 5 is carried by and extends laterally out of the handle piece 3, via which light guide connector 5 the instrument can be connected with a light source.

The illustrated instrument has three closure windows in all, namely a distal closure window 6, a proximal closure window 7 (ocular or eyepiece window) and also a lateral closure window 8 (illumination window). The closure windows 6, 7 and 8 may comprise the materials indicated in the summary above. In the present embodiment, they consist of spinel. As discussed below, any or all of the closure windows 6, 7 or 8 could alternately be a lens.

While the closure windows 6 and 8 are approximately cylindrical in construction and sit in a stepped frame 9, the ocular window 7 is soldered in directly, running conically toward the proximal instrument end and in the correspondingly formed eyepiece 4 using an active solder, such as, for example, Au/Cu/Ti or Ag/Cu/Ti. The distal closure window 6 and the lighting window 8 have been soldered directly under high vacuum into the respective frames 9. These frames 9 have then been welded, together with the respective window 6 or 8, to the adjoining component of the instrument. The weld seam is designated by 10 or 11, respectively.

Figure 2A:
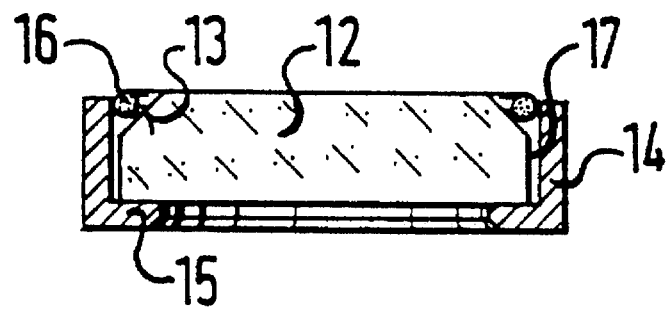
FIGS. 2a, b and c show an enlarged diagrammatic sectional representation of the process steps for the production of a distal closure window using a soldered/welded connection.
Figure 2B:
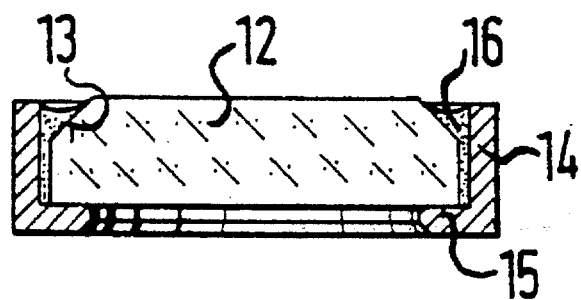
Figure 2C:
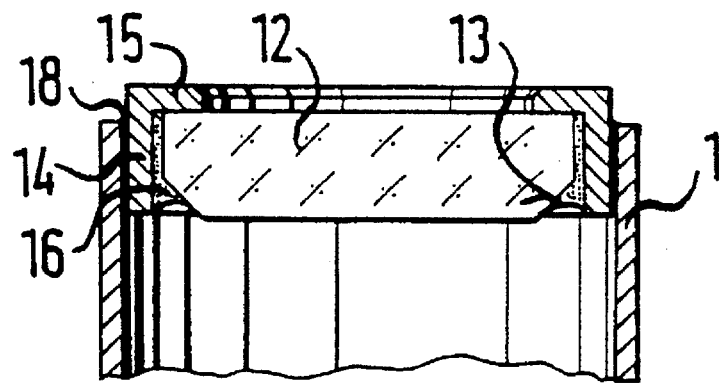

With the aid of FIGS. 2a to 2c, the production of a closure window is illustrated in detail, as used for example for forming the window 6 in FIG. 1. The actual window material is designated in FIG. 2 by 12 and consists of cubic monocrystalline spinel. This window material has a cylindrical form, in which one of the two contour edges is chamfered. The chamfer is designated by 13. The window material 12 lies with a small amount of play in a hollow cylindrical frame 14, which has on one side an extension or flange 15 forming a base, so that an L-section is produced, which can be seen from FIG. 2. The window material 12 lies in the frame 14 so that in the upper region between the window material 12 and the frame 14 a circumferential groove, approximately V-shaped in cross-section, is produced, which serves as a receptacle for solder. The solder material 16, represented here as an O-ring, lies in this groove.

The window, thus prefabricated, (frame, window material and solder material) is then subjected to a high vacuum soldering process, in which the solder material 16 flows into the capillary gap 17 between the frame 14 and window material 12 and thus connects these components firmly and tightly with each other. After this soldering process is completed, a component results, as illustrated in FIG. 2b. This component is then inserted into the actual endoscope shaft 1 and is welded tightly therewith on the edge, so that a unitary component configuration is produced, which can be seen with the aid of FIG. 2c. The weld seam is designated by 18 in FIG. 2c.

The windows shown in the drawing are planar. Alternatively, however, one or more of the windows, for example the eyepiece window or ocular, may be a lens, made of one of the materials referred to herein. Any such lens-form window may be in addition to, or take the place of, a corresponding (i.e., having the same function) component of the internal optical observation system (not shown) of the endoscope.

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the appended claims.

We claim:

1. In an endoscopic instrument including an elongated shaft, an optical observation system arranged therein, and at least one closure window, the shaft having at least one opening closed by said closure window which is firmly and tightly connected with the shaft, the improvement comprising the closure window being constructed of a material selected from the group consisting of spinel and yttrium-aluminum-garnet.

2. An endoscopic instrument according to claim 1, wherein the optical observation system is hermetically sealed by said at least one closure window.

3. An endoscopic instrument according to claim 1, wherein the material of said at least one closure window comprises cubic monocrystalline spinel.

4. An endoscopic instrument according to claim 1, wherein the material of said at least one closure window comprises polycrystalline spinel.

5. An endoscopic instrument according to claim 1, wherein the material of said at least one closure window comprises undoped yttrium-aluminum-garnet.

6. An endoscopic instrument according to claim 1, wherein the material of said at least one closure window comprises neodymium-doped yttrium-aluminum-garnet.

7. An endoscopic instrument according to claim 1, further comprising at least one metallic frame, the material of said at least one window being connected into said metallic frame by a solder joint, and said frame being connected to the instrument shaft by a weld seam.

8. An endoscopic instrument according to claim 7, wherein the solder joint is formed by high vacuum soldering.

9. An endoscopic instrument according to claim 7, wherein said frame is in the form of an annulus having an L-shaped cross section.

10. An endoscopic instrument according to claim 7, further comprising a capillary gap between an edge of said window and said frame, said gap being filled with solder.

11. An endoscopic instrument according to claim 7, further comprising a V-shaped groove between an upper region of said frame and an edge of said window for receiving a solder material which forms said solder joint.

12. An endoscopic instrument according to claim 11, wherein said solder joint is formed of said solder material which has flowed from said groove into a capillary gap between an edge of said window and said frame by means of high vacuum soldering.

13. An endoscopic instrument according to claim 1, wherein the material of said at least one window has a metallic coating at an edge of the window and the window is connected into the instrument by a solder joint.

14. An endoscopic instrument according to claim 1, wherein said closure window is a lens.

15. An endoscopic instrument according to claim 1, wherein the shaft has a distal end opening, and the closure window seals the distal end of the shaft.

16. An endoscopic instrument according to claim 1, wherein the shaft has a proximal end opening, and the closure window forms part of an eyepiece which closes the proximal end.

17. An endoscopic instrument according to claim 1, wherein the shaft has a lateral opening for a light guide, and the closure window seals the lateral opening.

* * * * *